(12) United States Patent
Griffin

(10) Patent No.: US 7,932,297 B2
(45) Date of Patent: *Apr. 26, 2011

(54) METHOD AND SYSTEM FOR PRODUCING ALTERNATIVE LIQUID FUELS OR CHEMICALS

(75) Inventor: Thomas Paul Griffin, Chadds Ford, PA (US)

(73) Assignee: Pennsylvania Sustainable Technologies, LLC, Bethlehem, PA (US)

( * ) Notice: Subject to any disclaimer, the term of this patent is extended or adjusted under 35 U.S.C. 154(b) by 111 days.

This patent is subject to a terminal disclaimer.

(21) Appl. No.: 12/353,702

(22) Filed: Jan. 14, 2009

(65) Prior Publication Data
US 2009/0182176 A1   Jul. 16, 2009

Related U.S. Application Data

(60) Provisional application No. 61/020,772, filed on Jan. 14, 2008.

(51) Int. Cl.
C07C 27/04 (2006.01)
(52) U.S. Cl. .................................. 518/702; 518/700
(58) Field of Classification Search .................. None
See application file for complete search history.

(56) References Cited

U.S. PATENT DOCUMENTS

| | | | |
|---|---|---|---|
| 4,825,013 | A | 4/1989 | Quarderer et al. |
| 5,013,407 | A | 5/1991 | Nocca et al. |
| 5,026,459 | A | 6/1991 | Quang et al. |
| 5,169,869 | A | 12/1992 | Miller et al. |
| 5,368,691 | A | 11/1994 | Asselineau et al. |
| 5,449,801 | A | 9/1995 | Barnum et al. |
| 5,615,561 | A | 4/1997 | Houshmand et al. |
| 5,703,133 | A | 12/1997 | Vanderspurt et al. |
| 5,866,095 | A | 2/1999 | McGeever et al. |
| 6,017,371 | A | 1/2000 | Gheysens et al. |
| 6,526,777 | B1 | 3/2003 | Campbell et al. |
| 6,673,845 | B2 | 1/2004 | Price |
| 6,676,716 | B2 | 1/2004 | Fujimura et al. |
| 6,723,886 | B2 | 4/2004 | Allison et al. |
| 6,742,358 | B2 | 6/2004 | Wilkinson et al. |
| 6,759,439 | B2 | 7/2004 | Chao et al. |
| 6,797,243 | B2 | 9/2004 | Arcuri et al. |
| 6,824,682 | B2 | 11/2004 | Branson |
| 6,872,753 | B2 | 3/2005 | Landis et al. |
| 6,889,523 | B2 | 5/2005 | Wilkinson et al. |
| 6,945,075 | B2 | 9/2005 | Wilkinson et al. |
| 6,956,063 | B2 | 10/2005 | Zhang et al. |
| 7,001,927 | B2 | 2/2006 | Zhang et al. |
| 7,010,937 | B2 | 3/2006 | Wilkinson et al. |
| 7,204,100 | B2 | 4/2007 | Wilkinson et al. |
| 7,210,311 | B2 | 5/2007 | Wilkinson et al. |
| 7,276,540 | B2 | 10/2007 | Espinoza et al. |
| 2006/0014841 | A1 * | 1/2006 | Melnichuk et al. .......... 518/726 |

FOREIGN PATENT DOCUMENTS

| | | | |
|---|---|---|---|
| FR | 2 571 719 | A1 | 4/1986 |
| WO | WO 2004/000723 | A1 | 12/2003 |
| WO | WO 2005/040392 | A1 | 5/2005 |
| WO | WO 2006/088462 | A1 | 8/2006 |
| WO | WO 2007/003899 | A1 | 1/2007 |
| WO | WO 2007/003909 | A1 | 1/2007 |

OTHER PUBLICATIONS

Berg, C., "World Fuel Ethanol Analysis and Outlook", archived at http://www.distill.com/World-Fuel-Ethanol-A&O-2004.html (2004).
Beretta, A., Qun Sun, R.B. Herman, and K. Klier, "Productlon of Methanol and Isobutyl Alcohol Mixtures over Cesium-Promoted Cu/ZnO/Cr$_2$O$_3$ and ZnO/Cr$_2$O$_3$ Catalysts", *Ind. Eng. Chem. Res.*, 35; 1534-1542 (1996).
BP Corporation Press Release. "Test Results Show Biobutanol Performs Similarly to Unleaded Gasoline", BP Corporation Press Release, Apr. 20, 2007; archived via *Green Car Congress* website: http://www.greencarcongress.com/2007/04/test_results_sh.html#more.
Herman R.G., "Advances in Catalytic Synthesis and Utilization of Higher Alcohols", *Catalysis Today*, 55, pp. 233-245 (2000).
Luyben, W.L., "Control of the Heterogeneous Azeotropic n-Butanol/Water Distillation System", *Energy & Fuels*, 22 (6), 4249-4256, Sep. 2008.
Minchener, A.J., "Coal Gasification for Advanced Power Generation," *Fuel*, 84; 2222-2235 2005.
Nunan, J.G., R.G. Herman and K. Klier, "Higher Alcohol and Oxygenate Synthesis over Cs/Cu/ZnO/M$_2$O$_3$ (M=Al, Cr) Catalysts", *Journal of Catalysis*, 116: 222-229 (1989).
Olson, E.S., R.K. Sharma and T.R. Aulich. "Higher Alcohols Biorefinery —Improvement of Catalyst for Ethanol Conversion," *Applied Biochemistry and Biotechnology*, 115; 913-932 (.2004).
Paul, Ratnasamy (2007) F-T proposal submitted to the National Centre of Catalysis Research (NCCR—India). NCCR Internal Bulletin (unpublished): archived at: http://203.199.213.48/1089/.

(Continued)

Primary Examiner — Brian J Davis
(74) Attorney, Agent, or Firm — Goodwin Procter LLP

(57) ABSTRACT

A method and system for the production of valuable chemicals or alternative liquid fuels via an integrated biomass conversion and upgrading process is disclosed. The process integrates three subcomponent processes, capturing the desirable attributes of each: zoned partial oxidation, alcohol production, and gas-to-liquids reformation. The method and system may include reacting gasification intermediates—e.g., syngas from zoned partial oxidation, with bioprocessing intermediates—e.g., aqueous ethanol from alcohol production in a reactive separation to produce a product(s) of higher alcohols, liquid hydrocarbons, or a combination of these. The product(s) can be split into two (or more) boiling point fractions by the same reactive separations unit operation. The resulting product(s) are valuable for a variety of applications, including potentially as alternative (non-fossil-based) liquid transportation fuels.

17 Claims, 1 Drawing Sheet

OTHER PUBLICATIONS

Pimentel, D., "Ethanol Fuels: Energy Balance, Economics, and Environmental Impacts are Negative", *Natural Resources Research*, 12, vol. 2. 127-134 (2003).

Roine, A., *HSC Chemistry ® 6.0*, Outokumpu Technology, Pori, Finland; ISBN-13: 978-952-9507-12-2; Aug. 2006.

Schobert, H.H, and C. Song, "Chemicals and Materials from Coal in the 21$^{st}$ Century," Fuel, 81; 15-32(2002).

Selinger et al.: "TwinRec Gasification and Ash Melting Technology —Now Established for Municipal Waste," 4$^{th}$ *International Symposium on Waste Treatment Technologies*, Sheffield, UK (2003).

Spath, P.L. and D.C. Dayton, *Preliminary Screening—Technical end Economic Assessment of Synthesis Gas to Fuels and Chemicals with Emphasis on the Potential for Biomass-Derived Syngas*; NREL/TP-510-34929, Dec. 2003.

van Heek, K.H., B.O. Strobel and W. Wanzl, "Coal Utilization Processes and their Application to Waste Recycling and Biomass Conversion." *Fuel*, 73(7). 1135-1143 (1994.

("8,000-year-old Wine Unearthed in Georgia"; London, UK, Dec 28. 2003 (author unknown)).

* cited by examiner

METHOD AND SYSTEM FOR PRODUCING ALTERNATIVE LIQUID FUELS OR CHEMICALS

This application claims priority to provisional application Ser. No. 61/020,772, entitled: "Method of Synthesis of Alternative Liquid Fuels via an Integrated Biomass Conversion and Upgrading Process," filed on Jan. 14, 2008, the disclosure of which is incorporated by reference. This application also is related to patent application Ser. No. 12/353,654, entitled: "Reactive Separation to Upgrade Bioprocess Intermediates to Higher Value Liquid Fuels or Chemicals," filed concurrently herewith, the disclosure of which is incorporated herein by reference.

BACKGROUND

1. Field of the Invention

Embodiments of the invention relate to methods and systems for producing valuable chemicals, such as alternative liquid fuels. Specific embodiments involve methods and systems for producing valuable chemicals that include the conversion of hydrocarbon-containing materials into valuable chemicals by subjecting at least a portion of the hydrocarbon-containing material to gasification/partial oxidation to produce synthesis gas ("syngas"), the syngas containing primarily carbon monoxide (CO) and hydrogen ($H_2$). The method and system also includes introducing at least an alcohol (in which the alcohol may be generated or otherwise derived through fermentation of a hydrocarbon-containing material) and the syngas to a reformer to generate saturated hydrocarbons, higher alcohols, or combinations thereof. The system includes the unit operations and process streams useful in carrying out the method.

2. Description of the Related Art

Alternative liquid transportation fuels could provide economic, security, and environmental benefits. Increased worldwide energy demands from countries such as India and China are likely to increase oil and fuel prices and may lead to new political conflicts. Further, carbon-based greenhouse gas emissions continue to accumulate in the atmosphere, and the industrialization of those populous countries likely will accelerate that accumulation. Transportation fuels derived from locally available inputs could reduce, or slow the growth in, demand for crude oil and help to mitigate these problems.

Transportation fuels derived from renewable biomass, or "biofuels," are of particular commercial interest. Biomass can be viewed as intermediate-term storage of solar energy and atmospheric carbon, via photosynthesis and carbon fixing mechanisms. With cultivation and harvesting cycles measured in months, biomass is, in principle, a renewable domestic energy resource.

The two most developed and commercially available, non-petroleum-based alternative fuels are biodiesel and bioethanol. For automotive transportation fuels, "bioethanol," or ethanol derived from biological sources, is the commercial leader. However, bioethanol's chemical and physical property deficiencies relative to conventional combustion fuels such as gasoline limit its attractiveness as a fuel. The volumetric energy density of ethanol is approximately 70% of typical unleaded gasoline products. In addition, the volatility and fugitive loss potential of ethanol is considerably higher. Carbohydrates such as sugars and simple starches are the biomass components most easily converted into ethanol. Corn, wheat, and sugar cane are the most commonly used crops and their use impacts food prices and availability. Finally, most automobiles have not been modified to run on bioethanol as a stand-alone fuel. Thus, bioethanol's use is currently limited to a low-percentage gasoline additive.

Simple alcohols can be manufactured through several processes. Methanol, for example, is commonly produced using natural gas reforming reactions; petroleum feedstocks also can be converted and reformed. Propanol and higher alcohols typically are produced from petrochemical sources, although some bioprocessing options are also becoming more viable. For ethanol, fermentation of sugars, either directly from sugar plants such as cane and beet, or indirectly, from sugars derived by saccharification of other carbohydrates such as corn grain and wheat grain is well-established and popular. The latter route, starting with corn, is the most common approach in the United States.

Fermentation science dates back eight millennia ("8,000-year-old Wine Unearthed in Georgia"; London, UK, Dec. 28, 2003 (author unknown)) and has long been practiced with only incremental improvements. While the scale of bioethanol facilities has increased (i.e., facilities now commonly have capacities of 100M gallons per year (gpy) in the US and more than 200M gpy in China), the basic chemical and biological processes remain the same. See Berg, C., "World Fuel Ethanol Analysis and Outlook", archived at http://www.distill.com/World-Fuel-Ethanol-A&O-2004.html (2004).

The long-standing limitations of fermentation from grain are well understood. These include: (i) energy intensity of the process; (ii) high water usage or water treatment burden; (iii) maximum theoretical utility of only 51% of the carbohydrate substrate, none from cellulose; (iv) economics dependent on a primary co-product of regional and seasonal value often called distiller's grains and solubles ("DGS"); if dried, dried distiller's grains and solubles ("DDGS"); and (v) consumption of valuable, food-chain capable, carbohydrate resources.

State-of-the-art fermentation processes yield a relatively dilute intermediate of typically 7-15% ethanol in water, along with a number of other byproducts. Energy-intensive distillation usually is required to concentrate and further purify the ethanol. In addition, physical separation approaches, such as phase separation and/or azeotropic distillation, are often used to overcome the well-known azeotrope between water and ethanol, which otherwise resists separation by simple distillation. As a result, the energy payback ratio, or the energy value of a product relative to the required process energy inputs, is typically close to, or even less than, break-even. Pimentel, D., "Ethanol Fuels: Energy Balance, Economics, and Environmental Impacts are Negative", *Natural Resources Research,* 12, vol. 2, 127-134 (2003).

It is hypothesized that a heavier range of chemicals, including both hydrocarbons and simple (mono) alcohols, might offer superior performance as fuel components, and greater chemical value in other applications. Significant biofuels research and development efforts therefore are being devoted to this hypothesis. For example, DuPont and BP have announced the pursuit of biological routes to butanol, or "biobutanol", as a preferred fuel supplement. Superior fuel performance of butanol relative to ethanol has been quantitatively supported by fuel property testing results. See BP Corporation Press Release, "Test Results Show Biobutanol Performs Similarly to Unleaded Gasoline", BP Corporation Press Release, Apr. 20, 2007; archived via Green Car Congress website: http://www.greencarcongress.com/2007/04/test_results_sh.html#more.

Even heavier alcohols (i.e., those heavier than butanol), and analogous hydrocarbons may be even more valuable as fuel replacements. Thus, mixtures of aliphatic hydrocarbons and some higher alcohol and/or ether species may be a more desirable synthetic fuel mixture for today's automotive engines. The advantages of such fuel mixtures have also been disclosed by Jimeson et al. (Standard Alcohol Company of America). Jimeson, R. M., Radosevich, M. C., and Stevens, R. R., "Mixed Alcohol Fuels for Internal Combustion Engines, Furnaces, Boilers, Kilns and Gasifiers," International Application under the Patent Cooperation Treaty (PCT), WO 2006/088462 A1; PCT Publ. Date Aug. 24, 2006, the disclosure of which is incorporated by reference herein in its entirety.

Beretta et al. also recognized a need to shift the fuel product MWD to higher species, and proposed a multi-step approach via dual-bed operations and further downstream processing. See Beretta, A., Qun Sun, R. B. Herman, and K. Klier, "Production of Methanol and Isobutyl Alcohol Mixtures over Cesium-Promoted Cu/ZnO/$Cr_2O_3$ and ZnO/$Cr_2O_3$ Catalysts", *Ind. Eng. Chem. Res.*, 35; 1534-1542 (1996).

The creation of the first C—C bond, the central bond in ethanol, is energetically the most difficult hurdle in these synthetic chemical pathways. Bell et al. acknowledged this limitation in alcohol synthesis from syngas, and taught a method of building up higher weight species via methanol synthesis, followed by continuous recycle with homologation. Bell, P. S., L. W. Bolton, B. P. Gracey, and M. K. Lee, "Process for the Conversion of Synthesis Gas to Oxygenates Containing $C_{2+}$ Alcohols", International Application under the Patent Cooperation Treaty (PCT), WO 2007/003909 A1; PCT Publ. Date Jan. 11, 2007, the disclosure of which is incorporated by reference herein in its entirety. Due to recompression in each recycle pass, this method is somewhat energy intensive and yields a substantial portion of residual methanol and an undesirable byproduct ester.

Gasification, a form of partial oxidation of feedstocks to yield a high value energy or chemical intermediate gas mixture, is one well-established approach to deriving energy values from solid hydrocarbons. Most of the existing technology base in gasification was developed for coal conversion. Coal gasification, using the integrated gasification/combined cycle (IGCC) approach, is a mature commercial technology in which coal is first converted into synthesis gas ("syngas"), a mixture primarily of carbon monoxide (CO) and hydrogen ($H_2$). This energy conversion option has been well documented by many authors and inventors; notable is the recent review by Minchener. Minchener, A. J., "Coal Gasification for Advanced Power Generation," *Fuel*, 84; 2222-2235 (2005). Extension of gasification technology to biomass feedstocks also has been well documented, for example by van Heek et al. van Heek, K. H., B. O. Strobel and W. Wanzl, "Coal Utilization Processes and their Application to Waste Recycling and Biomass Conversion," *Fuel*, 73(7); 1135-1143 (1994).

The syngas mixture that results from gasification processes can be used as a synthetic chemicals feedstock or, on very large scales, further converted through full oxidation in a gas turbine and steam recovery system. This approach captures value from the electrical output and the steam which can be used directly, or further converted into additional electric power. Due to limitations in gasification reactor performance, however, carbon dioxide and undesirable tar and oil fragments are common in the syngas mixture, as is the partial generation of methane ($CH_4$). Accordingly, available carbon is underutilized, and potential greenhouse gas (GHG) reductions are not realized. In addition, operational difficulties such as fouling and plugging occur, and the potential for emissions of hazardous trace gas pollutants increases.

For several decades, entrained flow gasifiers, particularly those of the high-temperature (>1200° C.) slagging type, have predominated gasification designs. Reactors with more homogeneous composition and temperature fields, most notably the fluidized bed gasification system, however, have been used and documented extensively in recent years. See, e.g., Selinger et al., "TwinRec Gasification and Ash Melting Technology—Now Established for Municipal Waste," $4^{th}$ *International Symposium on Waste Treatment Technologies*, Sheffield, UK (2003). The fluidized bed operates at lower average gasification temperatures (typically <1100° C.), reducing energy losses and increasing containment system lifetimes. It also has the potential for greater operational stability and robustness of process control, with respect to both physical and chemical forms and variances in the incoming feed.

Molten metal gasification technology, which has been used largely for waste conversion, offers benefits similar to those offered by the fluidized bed, such as increased control and stability. Its potential for biomass or other hydrocarbon conversion for advanced energy applications also is established in the patent literature. For example, McGeever and Nagel describe partial oxidation of hydrocarbons via a molten metal gasification system, yielding syngas which can be further transformed, as described previously. McGeever, C. E. and C. J. Nagel, "Method and System of Formation and Oxidation of Dissolved Atomic Constituents in a Molten Bath," U.S. Pat. No. 5,866,095, the disclosure of which is incorporated by reference herein in its entirety.

The importance and potential of the Fischer-Tropsch ("F-T") and related syntheses for alcohol derivation from biomass, including current industrial efforts to pursue these routes commercially, are detailed in the comprehensive review of Spath and Dayton of the National Renewable Energy Laboratory (NREL). Spath, P. L. and D. C. Dayton, Preliminary Screening—Technical and Economic Assessment of Synthesis Gas to Fuels and Chemicals with Emphasis on the Potential for Biomass-Derived Syngas; NREL/TP-510-34929, December 2003. A wide number of pathways are available, and many of these can be summarized in broad mechanistic groupings.

Reformation of syngas to aliphatic liquid hydrocarbons (suitable for various fuel applications), for example, was first pioneered by Fischer and Tropsch nearly a century ago. While this chemistry has been commercially practiced for decades, most notably by SASOL (South Africa), the coal-to-liquids approach has not held universal economic appeal. A review of the status and history of the Fischer-Tropsch synthesis (and related syntheses), as well as its place among similar or competing coal conversion strategies, was provided by Schobert and Song. Schobert, H. H. and C. Song, "Chemicals and Materials from Coal in the $21^{st}$ Century," Fuel, 81; 15-32 (2002).

Fischer-Tropsch catalysts and process schemes have a propensity to yield an exponential, Flory-Shultz product distribution, which includes a substantial fraction of lighter species, particularly methane. Paul, Ratnasamy (2007) F-T proposal submitted to the National Centre of Catalysis Research (NCCR—India). NCCR Internal Bulletin (unpublished); archived at: http://203.199.213.48/1089/. Similarly, in alcohol production via syngas homologation, methanol ($CH_3OH$) is the primary product, unless significant and energy-intensive intermediate recycle is used. Since methanol, similar to ethanol, has physical property shortcomings relative to gasoline, the use of this route to generate these chemicals has been limited.

"Higher alcohols," those heavier than methanol or "$C_{2+}$" alcohols, also can be accessed by catalytic mechanisms that are similar to and derived from the Fischer-Tropsch route. One higher alcohol pathway that has been investigated is "aldol coupling with oxygen retention reversal", documented by Nunan et al., among others. Nunan, J. G., R. G. Herman and K. Klier, "Higher Alcohol and Oxygenate Synthesis over Cs/Cu/ZnO/$M_2O_3$ (M=Al, Cr) Catalysts," Journal of Catalysis, 116; 222-229 (1989). In this route higher alcohols are generated via chain growth of smaller, primary alcohols, through condensation with dehydration. The analogous condensation reaction between methanol and ethanol is also of interest because of established routes to each reactant from biomass. This is described as the Guerbet Reaction pathway, yielding propanol and heavier alcohols through the "Higher Alcohol Biorefinery" concept of Olson et al. Olson, E. S., R. K. Sharma and T. R. Aulich, "Higher Alcohols Biorefinery—Improvement of Catalyst for Ethanol Conversion," Applied Biochemistry and Biotechnology, 115; 913-932 (2004).

Interest in generation of oxygenated hydrocarbon chemicals, most notably as fuel components, was pursued by Gheysens et al. in the post-F-T synthesis of light ethers. Gheysens, J.-L. G. et al., "Composition and method for producing a multiple boiling point ether gasoline component," U.S. Pat. No. 6,017,371; Jan. 25, 2000, the disclosure of which is incorporated by reference herein in its entirety. Analogous synthesis of light branched alcohols, or "isoalcohols", was developed by Vanderspurt et al., in addition to the researchers cited earlier in this field. Vanderspurt, T. H. et al., "Isoalcohol synthesis", U.S. Pat. No. 5,703,133; Dec. 30, 1997, the disclosure of which is incorporated by reference herein in its entirety. A wider range of possible feedstocks, including wastes, was applied by Fujimura et al. Fujimura, H. et al., "Method and apparatus for treating wastes by gasification", U.S. Pat. No. 6,676,716; Jan. 13, 2004, the disclosure of which is incorporated by reference herein in its entirety.

Landis et al. described the pursuit of two product types in tandem, from F-T routes, broadly in terms of hydrocarbons and oxygenates. Landis, S. R. et al., "Managing hydrogen and carbon monoxide in a gas to liquid plant to control the H2/CO ratio in the Fischer-Tropsch reactor feed", U.S. Pat. No. 6,872,753; Mar. 29, 2005, the disclosure of which is incorporated by reference herein in its entirety. Miller et al., and its precursors, taught the synthesis of higher alcohols from syngas over a mixed Cu—Cr oxide catalyst. Miller, J. T. et al., "Catalytic process for producing olefins or higher alcohols from synthesis gas," U.S. Pat. No. 5,169,869; Apr. 28, 1992, the disclosure of which is incorporated by reference herein in its entirety. Earlier, Quarderer et al. described the use of "lower alcohols" and syngas to generate higher alcohols, specifically over a Mo-based catalyst, without specifying equipment or reaction engineering details. Quarderer, D. J. et al., "Preparation of ethanol and higher alcohols from lower carbon number alcohols", U.S. Pat. No. 4,825,013; Apr. 25, 1989, the disclosure of which is incorporated by reference herein in its entirety.

Energy integration advantages were allegedly captured by Price in the form of electric power. Price, J. G., "Production of hydrocarbon products", U.S. Pat. No. 6,673,845; Jan. 6, 2004, the disclosure of which is incorporated by reference herein in its entirety. Energy integration advantages also were allegedly realized by Arcuri et al. in the form of thermal energy integrated within FT hydrocarbon synthesis reactions. Arcuri, K. B. et al., "Structured Fischer-Tropsch catalyst system and method", U.S. Pat. No. 6,797,243; Sep. 28, 2004, the disclosure of which is incorporated by reference herein in its entirety. Allison et al. pursued reactive distillation process simplification in the synthesis of methanol. Allison, J. D. et al., "Use of catalytic distillation reactor for methanol synthesis", U.S. Pat. No. 6,723,886; Apr. 20, 2004, the disclosure of which is incorporated by reference herein in its entirety.

Upgrading of alcohols or other intermediates from bioprocesses might be accomplished in a variety of different heterogeneous reactor configurations. Gracey and Bolton have disclosed the use of reactive distillation in the synthesis of light olefins from alcohols. Gracey, B. P. and L. W. Bolton, "Reactive Distillation for the Dehydration of Mixed Alcohols", International Application under the Patent Cooperation Treaty (PCT), WO 2007/003899 A1; PCT Publ. Date Jan. 11, 2007, the disclosure of which is incorporated by reference herein in its entirety.

An additional limitation of both existing fermentation processes, and high-temperature thermal processes, such as gasification, is that energy released during processing is not effectively captured or otherwise integrated to the process scheme. In particular, the separation, concentration and purification of ethanol from a dilute fermentation broth, is quite energy intensive—a factor which can greatly limit, or even eliminate, any net energy gain ("energy payback") associated with bioethanol production. Pimentel, D., "Ethanol Fuels: Energy Balance, Economics, and Environmental Impacts are Negative", *Natural Resources Research*, 12, vol. 2, 127-134 (2003).

In summary, there are several shortcomings associated with current processes to derive select chemicals, for example, liquid fuels from biomass or other abundant non-petroleum resources. Fermentation is practical only for ethanol production from grain-derived carbohydrates. It consumes significant energy, faces substantial challenges regarding water management, and converts less than half the available carbon into fuel. Additionally, ethanol has limited use as a chemical feedstock, as well as drawbacks (e.g., low energy density, high fugitive loss potential, and difficult phase behavior with water) when used as a fuel. Further, Fischer-Tropsch and related syntheses (the primary alternative routes to produce chemicals and fuels from these feedstocks) offer limited selectivity to desired chemical (or fuel) species, with challenges of control, in terms of heat removal and stability of the resulting product mix (e.g., molecular weight distribution).

The description herein of advantages or disadvantages of certain methods and systems is not intended to limit the various embodiments disclosed herein to either their inclusion or exclusion. Indeed, certain embodiments may include one or more known systems or methods, without suffering from the disadvantages described herein.

SUMMARY OF EXEMPLARY EMBODIMENTS

Various embodiments of the present invention enable the synthesis of valuable chemicals that could, for example, serve as liquid fuel components or fuel substitutes, while using non-food such as inedible biomass inputs to derive a significant portion of the product. Some of the embodiments of the invention circumvent the complexity of known multi-step approaches, for example, using dual beds, and take advantage of established fermentation processing for a similar purpose: overcoming the activation energy barrier in the initial pathway, establishing the initial C—C bond framework, and thus facilitating the remainder of the pathways to higher alcohol synthesis. The result is a process that could be used to overcome existing biofuels deployment limitations, (some of which are described above), thereby allowing for more complete use of available biomass (i.e., beyond carbohydrates), and yielding liquids that can serve more completely as improved fuel substitutes, or industrial chemicals, and that have more attractive commercial attributes.

One exemplary aspect of the embodiments is that it integrates three subcomponent processes to create higher value chemicals, capturing the benefits of each: gasification, alcohol production (alcohol generation and primary separations), and gas-to-liquids reformation (reactive separation). The first two subcomponent processes produce intermediate feed streams for introduction into the reactive separation phase: (a) syngas (via gasification); and (b) simple alcohols (from alcohol production). These two intermediate streams then can be combined and upgraded through a reactive separation operation. The process and system of the embodiments yields useful and valuable chemicals (suitable as liquid fuel components), such as, for example, higher alcohol(s) ($C_{2+}$ primary, secondary, or tertiary alcohols), and/or aliphatic liquid hydrocarbon(s) ($C_{4+}$ linear or branched saturated alkanes). Either of these two product types can be divided into two or more boiling point fractions by the same reactive separations unit operation. Mixtures of both types also can be produced. The integrated process thus yields a product of higher saturated alcohol(s), liquid aliphatic hydrocarbon(s), or a combination (and preferably blend) of these products for use, for example, as fuel components.

As described previously, there are several shortcomings associated with current processes to derive select chemicals—for example, liquid fuels—from biomass or other abundant non-petroleum resources. Fermentation is practical only for ethanol production from grain-derived carbohydrates. It consumes significant energy, faces substantial challenges regarding water management, and converts less than half the available carbon into fuel. Additionally, ethanol has limited use as a chemical feedstock, as well as drawbacks (e.g., low energy density, high fugitive loss potential, and difficult phase behavior with water) when used as a fuel. Further, Fischer-Tropsch and related syntheses (the primary alternative routes to produce chemicals and fuels from these feedstocks) offer limited selectivity to desired chemical (or fuel) species, with challenges of control, in terms of heat removal and stability of the resulting product mix (e.g., molecular weight distribution). The embodiments of the invention deliver process improvements that mitigate these shortcomings and deliver product(s) with more attractive commercial attributes.

It is to be understood that both the foregoing general description of the invention and the following detailed description are exemplary, but are not restrictive, of the invention.

BRIEF DESCRIPTION OF THE DRAWINGS

A more complete appreciation of the invention and many attendant advantages thereof will be readily obtained as the same becomes better understood by reference to the following detailed description when considered in connection with the accompanying drawing, in which.

DETAILED DESCRIPTION

Figure 1:
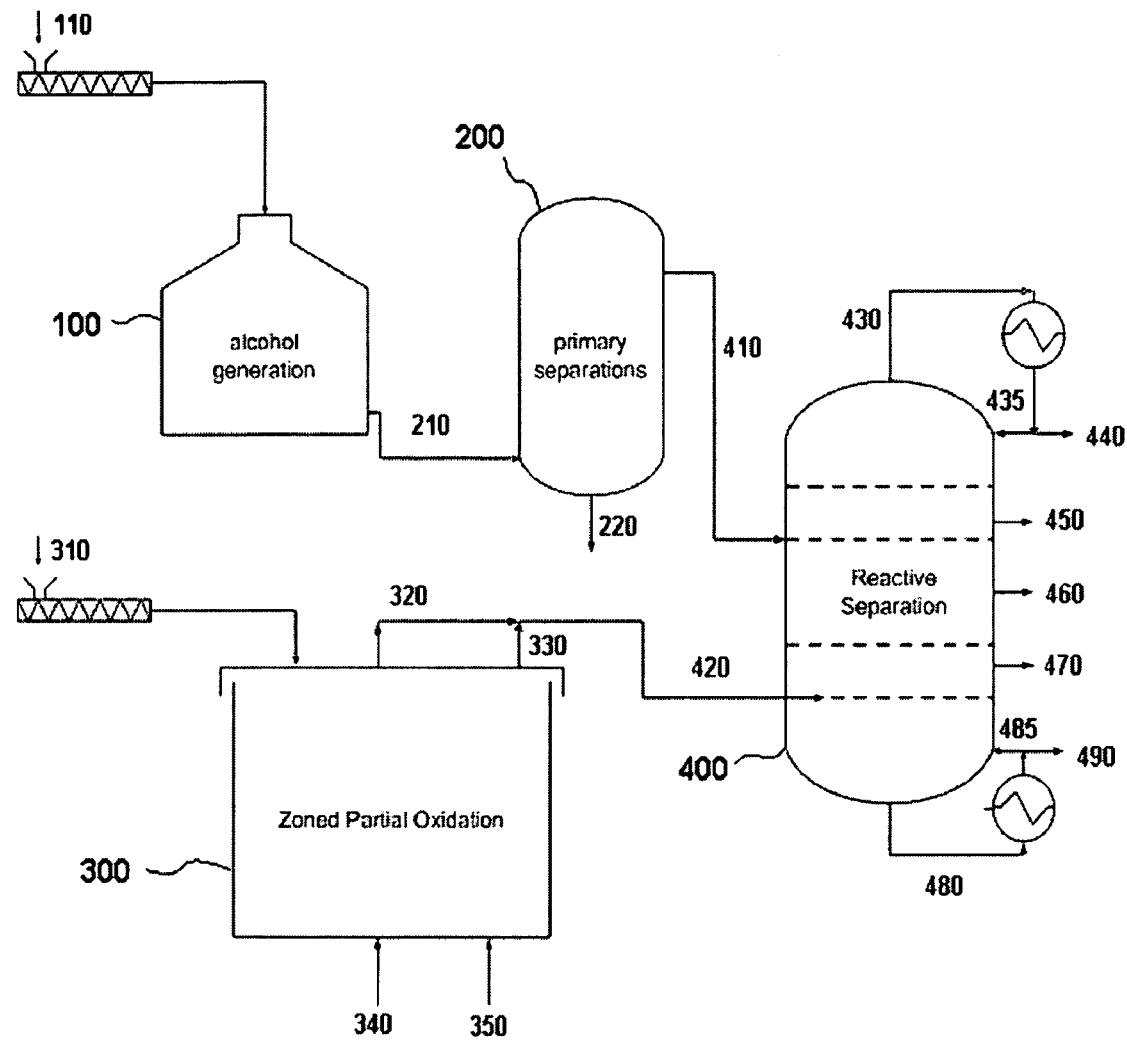
FIG. 1 illustrates a schematic representation of the integrated process for making valuable chemicals from hydrocarbon-containing materials.

Throughout this description, the expressions "hydrocarbon product" or "oxygenated hydrocarbon product" denote products that have at least one hydrogen atom and one carbon atom, or products that have at least one hydrogen atom and one carbon atom in which at least one hydrogen atom has been replaced with an oxygen-containing moiety, respectively. Preferably, the hydrocarbon product(s) include(s) one or more of: alkanes (normal or branched; aliphatic or cyclic), olefins (normal or branched), cyclic aromatics, and molecules with combinations of these moieties. Preferably, the oxygenated hydrocarbon product(s) include(s) one or more of: simple alcohols (normal or branched; aliphatic or cyclic), poly-alcohols (normal or branched, aliphatic or cyclic), normal or branched ethers (aliphatic or cyclic), normal or branched poly-ethers (aliphatic or cyclic), simple or poly-ketones (aliphatic or cyclic), simple or poly-aldehydes (aliphatic or cyclic), simple or poly-esters (aliphatic or cyclic), and molecules with combinations of these moieties.

Throughout this description, the expression "higher alcohols" denotes an alcohol having two or more carbon atoms ($C_{2+}$ primary, secondary, or tertiary saturated alcohols, or combinations thereof). Similarly, throughout this description, the expression "higher aliphatic hydrocarbons" denotes $C_{4+}$ saturated straight-chain or branched aliphatic hydrocarbons, or combinations thereof.

Throughout this description, the expression "higher value liquid fuel or chemical" denotes a liquid fuel or chemical that is worth more to consumers than the entity to which it is compared. For example, if the process or system starts with a bioprocess intermediate in the form of diluted bioethanol, that diluted bioethanol can be converted to a higher value liquid fuel or chemical by conversion to a liquid fuel, such as a higher alcohol that is worth more than diluted bioethanol. "Worth" in the context provided here denotes overall worth and not simply monetary value (e.g., it takes into consideration efficiency, consumption, environmental value, etc.).

A method and system is described herein that employs, as one feature, a gasification method to produce syngas that captures the operability, energy efficiency, controllability and robustness with respect to feed variability of advanced gasification systems such as a fluidized bed, or molten metal gasification. Thus, a feature of an embodiment of the invention improves carbon utility, and yields more pure intermediate species. This feature facilitates downstream processing while reducing the negative impact of unwanted byproducts. This gasification method is referred to herein as zoned partial oxidation. Throughout this description, the expression "zoned partial oxidation" denotes an operation that accomplishes the chemical conversion of hydrocarbons or hydrocarbon-containing material, and/or oxygenated hydrocarbons or oxygenated hydrocarbon-containing material, in two or more distinct physical regions (zones), resulting in a product with its overall carbon content predominantly in the form of carbon monoxide (CO), and its overall hydrogen content predominantly in the form of hydrogen gas ($H_2$).

One embodiment of the invention integrates three subcomponent processes to create higher value chemicals, capturing the benefits of each: zoned partial oxidation, alcohol production (alcohol generation and primary separations), and gas-to-liquids reformation (reactive separation). The first two subcomponent processes produce intermediate feed streams for introduction into the gas-to-liquids reformation (reactive separation) phase: (a) syngas (via zoned partial oxidation); and (b) simple alcohols or poly-alcohols (from alcohol production). These two intermediate streams then can be combined and upgraded through a reactive separation operation. The process and system of the embodiments yields useful and valuable chemicals (suitable as liquid fuel components), such as, for example, higher alcohol(s) ($C_{2+}$ primary, secondary, or tertiary alcohols), and/or aliphatic liquid hydrocarbon(s) ($C_{4+}$ linear or branched saturated alkanes). Either of these two product types can be divided into two or more boiling point fractions by the same reactive separations unit operation. Mixtures of both types also can be produced. The integrated process thus yields a product of higher saturated alcohol(s), liquid aliphatic hydrocarbon(s), or a combination (and preferably blend) of these products for use, e.g., as fuel components.

In one exemplary aspect of the embodiments, the zoned partial oxidation operation includes a gasification or partial oxidation reaction used to produce syngas that can be performed using either a molten metal system, or a fluidized bed system. The latter provides operation at a lower average gasification temperature (typically <1100° C.), reducing energy losses and increasing containment system lifetimes. Both provide the potential for greater operational stability and robustness of process control with respect to both physical and chemical forms and variances in the incoming feed.

In yet another exemplary aspect of the embodiments, the hydrocarbon input to the system may include carbon-containing waste or biomass, including, for example, waste plant material, industrial and municipal waste, human and animal waste, and the like. This enables use of low-cost non-food and non-petroleum resources in order to produce higher value liquids.

In yet another exemplary aspect of the invention, the feed for syngas production or alcohol generation can be equipped to handle bulk solids (solids greater than 1 mm in meandiameter) into the system. This can be accomplished using a variety of known methods in the field such as an auger or conveyor belt, along with for example a lock-hopper, or pressure-driven or piston-driven injection system. This allows the system to handle a wider variety of inputs to ultimately convert to higher value liquids. In the alcohol generation subcomponent process, the primary separations step provides in part for the removal of a portion of residual solids prior to the final gas-to-liquids reformation (reactive separation) process.

In yet another exemplary aspect of the embodiments, generation of the syngas may be accomplished with zoned partial oxidation, which comprises gasification or partial oxidation reactions in at least two stages. The first stage (or zone) accomplishes devolatilization or pyrolysis and, optionally, some degree of partial oxidation of the feed or devolatilization or pyrolysis intermediates. The second (and optionally third) stages (or zone(s)) generate(s) synthesis gas through partial oxidation.

In yet another exemplary aspect of the embodiments, the zoned partial oxidation step can further accept additional input streams to produce syngas. These inputs can be any hydrocarbon-containing material including solids by-products derived from the fermentation of biomass, aerobic or anaerobic digestion of biomass, hydrocarbon containing waste materials from available by-product streams or any carbon- or hydrogen-rich materials. This allows the syngas product to be fine tuned via the introduction and combination of these additional feeds. In addition, this enhances the overall process efficiency by allowing waste or by-product streams to be converted into syngas for use in reactive separation.

In yet another exemplary aspect of the embodiments, a control feedback loop may be utilized to better control the higher value liquid output. This can be accomplished by allowing the syngas product to be combined with the alcohol intermediate streams in appropriate ratios, and in particular, for the syngas product composition to be tailored specifically in terms of its $H_2/CO$ ratio prior to gas-to-liquids reformation (reactive separation). The liquid product composition(s) are monitored and maintained or adjusted via a feedback loop that can respond by altering the rates and ratio of the input streams to the zoned partial oxidation process for this purpose.

In yet another exemplary aspect of the embodiments, the gas-to-liquids reformation process of reaction and separation can be accomplished in a single unit operation. Ideally, reactive distillation is utilized as the separating process to upgrade the chemical or fuel value of a bioprocessing intermediate along with a separately-sourced syngas, CO, $H_2$, or other bioprocessing intermediate (or any combination thereof). Utilizing reactive distillation affords intraprocess energy and water management integration, thus greatly enhancing the efficiency of the overall process.

Particularly preferred embodiments now will be described with reference to the drawings attached hereto. Alcohol production, or alcohol generation and primary separations, preferably yields one of the two major reagents used in the reactive separation operation. A feed stream 110 containing a combination of hydrocarbon materials can be fed into the alcohol generation unit 100. In a preferred embodiment, these hydrocarbon materials undergo fermentation in the alcohol generation unit 100 to yield an alcohol-water, preferably bioethanol-water intermediate stream 210.

The alcohol-water intermediate stream 210 then can be fed into a primary separations unit 200 where it is subjected to removal of some of the water from the fermentation broth, along with residual solids. In a preferred embodiment, this mixture of water and fermentation solids (either dissolved, partially in suspension, and/or in slurry) can be removed in stream 220. The solids component in solids stream 220 can be processed into dried distiller's grains ("DDG"). While not necessary to the embodiment, the water is typically recovered, treated and recycled to fermentation. An alternative use of the DDG by-product is as a feed component for zoned partial oxidation (discussed below). Recovery and treatment for reuse and/or intraprocess recycle of both the water and DDG components are each accomplished through established operations.

The liquid output from the primary separations unit 200, stream 410 includes an aqueous, bioprocess intermediate. This aqueous bioprocess intermediate typically comprises at least one simple (mono-) alcohol, or a poly-alcohol, species. In a preferred embodiment, alcohol production is through fermentation, which will produce stream 410 as an ethanol-rich feed stream.

A second input stream to the reactive separation process 400 preferably is a syngas stream. Syngas typically is produced by feeding a separate hydrocarbon-containing stream 310 into the zoned partial oxidation unit 300. Stream 310 may include any of the following feedstocks, or mixtures of any subset thereof: (a) additional biomass—e.g., cellulose and/or lignin, whether associated with or cultivated with the carbohydrate sources or not, whether handled without chemical treatment or as a byproduct of separate chemical processing, e.g., pulp and paper processing; (b) solid byproducts from fermentation—e.g., DDG as described above; (c) DDGS, a mixture of DDG and stillage-derived solubles, a co-product commonly derived from fermentation operations not described herein; (d) hydrocarbon-containing co-feeds such as coal, petroleum coke, natural gas, recycled plastics; or (e) other organic, or organic-containing waste materials from industrial operations, municipal operations, humans, animals, or plants. In a preferred embodiment, stream 310 is a wide range of hydrocarbon and/or hydrocarbon-containing feedstocks, including non-fermentable and/or non-soluble biomass.

The proposed zoned partial oxidation operation 300 preferably includes at least two zones, and in a more preferred embodiment, at least three zones. The first zone accomplishes devolatilization or pyrolysis, and optionally some degree of partial oxidation. The subsequent one or more zone(s) accomplish(es) or complete(s) the syngas generation via partial oxidation of the feed and/or devolatilization or pyrolysis intermediates. In the case of at least three zones, respectively, these three zones accomplish devolatilization or pyrolysis, generation of a hydrogen ($H_2$)-rich syngas intermediate stream 320—with $H_2$—CO ratio greater than 1:1—and generation of a CO-rich syngas intermediate stream 330—with $H_2$—CO ratio less than 1:1.

The syngas intermediate(s)—stream 320 or stream 330 (two zone case), or in the preferred embodiment, a selected recombination of streams 320 and 330 (three zone case), yields the syngas or combined syngas stream, stream 420, which then may be subjected to the reactive separation operation 400. In the preferred case of the three-zone zoned partial oxidation operation, intermediate streams 320 and 330 are first recombined in an appropriate ratio to meet the intended product liquids composition streams 450 and 460 and relative yields.

Either or both of these chemical process and/or bioprocess intermediate streams (syngas, light alcohols) are deployable as co-feed(s) to the liquids upgrading reactive separation operation 400. The result is high process flexibility and the ability to utilize a broad range of hydrocarbons and/or hydrocarbon-containing resources in the production of fuel or chemical products.

This zoned processing (zoned partial oxidation) in partial oxidation unit 300 can be controlled by determination of product quality, molecular weight distribution, and relative splits among product liquid or gas species in streams 450 and 460. The input for this control scheme preferably is the real-time measurement of (a) intermediate product liquid or gas composition of streams 450 and 460, (b) $H_2$ and CO generation rates and/or $H_2$/CO ratio within one or more zones of the zoned partial oxidation, (c) carbon inventory within one or more zones of the zoned partial oxidation, or (d) a combination of two or more of these measureable indices. Those having ordinary skill in the art will be capable of designing a suitable control scheme to produce a wide variety of streams 450 and 460, or combinations thereof, using the guidelines provided herein.

To facilitate tailoring the composition and relative yields of ultimate product streams 450 and 460, zoned partial oxidation co-feed(s) and/or additional oxygen source(s) can optionally be charged to the zoned partial oxidation operation 300. The first co-feed, shown as stream 340, can either be hydrogen-rich or carbon-rich, relative to the main feed component(s). Some examples of hydrogen-rich co-feeds include steam, methane, natural gas, propane, or hydrogen gas. Some examples of carbon-rich co-feeds include coal, coke, or pitch. The second co-feed, shown as stream 350, is intended to be an oxidant relative to the conditions in the zoned partial oxidation reactor system 300. Typical examples of stream 350, when used, include oxygen, air, steam/water, or carbon dioxide.

The resultant syngas stream from zoned partial oxidation 300 is stream 420, which along with stream 410, is injected and processed via the reactive separations operation 400. The two streams may be combined prior to injection, or in the reactive separation unit 400 to produce either higher alcohol(s) ($C_{2+}$ primary, secondary, or tertiary saturated alcohols, or any combination of these) or higher aliphatic hydrocarbon(s) ($C_{4+}$ saturated straight-chain or branched aliphatic hydrocarbons, or a combination of these) product stream(s), or any combination of both products.

In a preferred embodiment this reactive separation can be accomplished by reactive distillation. This preferred process can yield useful and valuable liquid products (suitable as fuel components)—higher alcohol(s) ($C_{2+}$ primary, secondary, or tertiary alcohols), and/or aliphatic liquid hydrocarbon(s) ($C_{4+}$ linear or branched saturated alkanes). Either of these two products can be divided into two (or more) boiling point fractions by the same reactive separations unit operation 400; these fractions are depicted as streams 450 and 460, as will be described subsequently. Optionally, mixtures of both types also can be produced.

There are two potential reaction systems that can be employed in the reactive separation operation 400: (a) synthesis via condensation coupling to yield higher alcohols; or (b) synthesis of liquid hydrocarbons. Option (a) yields a range of alcohols, starting in molecular weight distribution (MWD) with ethanol (i.e., ethanol and heavier alcohols, or "$C_{2+}$" alcohols—preferably butanols and heavier alcohols, or "$C_{4+}$" alcohols). These can include primary, secondary, and tertiary saturated alcohols, or combinations thereof. Option (b) is most typically a Fischer-Tropsch or related synthesis of aliphatic liquid hydrocarbons, specifically starting in MWD with butanes (i.e., butanes and heavier saturated linear and branched aliphatic hydrocarbons or combinations thereof, or "$C_{4+}$" aliphatic hydrocarbons).

The reformation chemistry carried out in the reactive separation operation 400 thus is capable of generating: (a) higher alcohols, i.e., $C_{2+}$ primary, secondary, and/or tertiary saturated alcohols; (b) aliphatic liquid hydrocarbons, i.e., $C_{4+}$ saturated linear and/or branched liquid aliphatic hydrocarbons; or (c) mixtures of these two classes. These can be accomplished either individually or together (e.g., through parallel reformation operations utilizing parallel reactive separation process trains).

The preferred embodiments include chain growth initiated by the reaction between a primary alcohol and syngas (which includes at least one molar equivalent of carbon monoxide, relative to the alcohol). Additional chain growth then can involve the new alcohol and additional syngas (which includes at least one molar equivalent of carbon monoxide, relative to the alcohol), or reaction between two alcohol molecules, or a combination of these reaction pathways occurring in parallel. These parallel reactions are capable of yielding a higher alcohol mix, with the resultant molecular weight distribution (MWD) of the product mixture dependent on input species and quantities, as well as temperature, pressure, residence time and other reaction conditions.

In the preferred embodiments, the exotherm (energy release) generated by the higher alcohol synthesis reaction, along with a portion of the energy embodied in the high-temperature zoned partial oxidation output—carried with the syngas intermediate—drives the reactive separation operations unit 400, and provides energy required for the continuous separation, (e.g., as achieved in a reactive distillation column).

In a further preferred embodiment, the reactive separation operation 400 includes a region or stage for slurry-phase or other well-mixed heterogeneous catalytic liquids upgrading reaction(s), which is operated in tandem with the remaining regions or stages of the reactive separations operation. In another preferred embodiment, water is generated by a variety of reaction mechanisms with water rejection, in addition to water that was initially present in the bioprocess stream(s) as a diluent. Preferably, the water is generated within the well-mixed heterogeneous catalytic reaction region or stage of the reactive separation unit 400 operation. In this zone, the desired product molecular weight growth and oxygen removal (as a component of water) are both initiated. The hydrocarbons or oxygenated hydrocarbons can be simultaneously concentrated in an organic product phase via this removal of water. Preferably, this well-mixed heterogeneous catalytic reaction region or stage is near the bottom of the reactive separation unit 400 operation when that unit operation is disposed vertically, as shown in the drawings (although vertical orientation is not required). Using the guidelines provided herein, a person having ordinary skill in the art is capable of determining where this well-mixed heterogeneous catalytic reaction region or stage is located depending on the vapor-liquid equilibrium (VLE) behavior of the reacting components, the chemical makeup of the intermediates, temperature, pressure, the composition of the intended product stream(s), as well as engineering associated with tray or stage design and placement and number of stages or trays.

A water-rich stream 470 preferably is disengaged from the organic product phase and purged from the system either immediately at the material inlet stage or region of the reactive separations unit 400 operation, or in a distinct stage or region in a specific location within the reactive separations unit 400 operation. In a preferred embodiment, the exact location of this water-rich draw (i.e., withdrawal of the water-rich stream 470) will depend upon, for example, the vapor-liquid equilibrium (VLE) behavior of the reacting components, reaction intermediates, and the composition of the intended product stream(s), as well as engineering associated with tray or stage design and placement, and the specification of temperature and pressure over the full trajectory of all the stages or regions. The phase separation stage or region thus facilitates removal of a water-rich phase or stream 470 from the reactive slurry or liquid, and the transfer or return of the organic-rich phase to further regions or stages of the reactive separation for continued desired reaction(s) and/or rectification.

In another preferred embodiment, the reactive separation unit 400 operation further incorporates an interstage pressure drop, nozzle arrangement, or isenthalpic flash that facilitates aqueous-organic phase disengagement and separation, and the removal of water or a water-rich phase. This can be situated either at the same location as the well-mixed region or stage, or at an intermediate region or stage in the reactive separation unit 400 operation, i.e., in tandem with organic phase rectification. Interstage pressure drops, specific nozzle arrangements useful in accomplishing the desired disengagement and separation, and isenthalpic flash processes are known to those skilled in the art, who by using the guidelines provided herein, are capable of using such processes or apparatus to produce the desired result. For example, isenthalpic flash processes typically are used in liquefaction of natural gas, as disclosed in, for example, U.S. Pat. Nos. 7,210,311, 7,204,100, 7,010,937, 6,945,075, 6,889,523, 6,742,358, 6,526,777, and 5,615,561, the disclosures of which are incorporated by reference herein in their entirety.

The resultant organic-rich phase continues to react in the rectification zone(s) of the integrated reactive separation unit 400 operation, either through the same reactions or additional chain-growth, and/or dehydration reactions. In the preferred embodiment, the reactive separation is accomplished as a reactive distillation—with simultaneous molecular weight increase, oxygen reduction (as a component of water), water removal, and organic product rectification.

In a preferred embodiment, gases are transported upward, by momentum and/or buoyancy, within the reactive separations unit 400 as shown vertically oriented (reactive separation unit 400 also may be oriented at an angle, or on its side, as will be appreciated by those skilled in the art). Overhead vapors 430 are condensed and split as needed into reflux 435 or light product removal and/or purge 440. Likewise at the bottom of the reactive separation unit 400, the condensed mixture 480 is sent to the reboiler for return to the column 485 or liquid removal and/or purge 490.

The reactive separation operation 400 allows for two or more boiling point fractions of each product type 450, 460 to be drawn via side streams from the rectification stage(s). The process thus yields higher alcohol(s), liquid hydrocarbon(s), or a combination (and preferably blend) of these chemicals, with a particular application as fuel components. Adjusting product composition through co-feed control strategies, and via controlled combination of the component product cuts, delivers a stand-alone fuel product that can serve as either a gasoline replacement or additive.

Particularly preferred operating conditions and process stream compositions include the following. The reactive separation unit 400 preferably is operated at a temperature within the range of from about 200 to about 450° C., more preferably from about 250 to about 400° C., and most preferably from about 280 to about 350° C. The reactive separation unit 400 preferably is a reactive distillation unit capable of operating in two preferred modes. The first mode is a saturated VLE over all stages in which the absolute pressure is from about 1 to about 80 atmospheres (atm.), preferably from about 10 to about 70 atm., and most preferably from about 20 to about 50 atm. The number of stages in this first mode preferably is from 3-20, more preferably from about 5 to about 15 and most preferably from about 7 to about 12.

The second mode of operation of reactive separation unit 400 includes a pressurized feed/lowest stage(s); pressure letdown (e.g., flash) to upper, lower pressure, vapor only stages. In this mode, the number of lowest stages is from about 1-5, preferably 1-3, and most preferably 1-2, in which the pressure may range from about 1 to about 80 atm., preferably from about 10 to about 70 atm., and most preferably from about 40 to about 60 atm. The number of upper stages preferably is from about 3-15, preferably from about 5-12, and most preferably from about 6-10, in which the pressure may range from about 1 to about 80 atm., preferably from about 1 to about 40 atm., and most preferably from about 1 to about 20 atm.

The feed compositions to reactive separation unit 400 include the bioprocess intermediate stream 410 and the syngas 420. Bioprocess intermediate stream 410 preferably comprises aqueous alcohol, poly-alcohols, or mixtures of one or more of the two. The typical primary component in bioprocess intermediate stream 410 is ethanol, from fermentation, or alcohol generation unit 100. The composition of this stream, following fermentation and primary separations 200 (some water removal; solids removal) is a stream having from about 10-75% ethanol, preferably 15-60% ethanol, and most preferably 30-50% ethanol, by weight, with the balance being primarily water. Other possible primary components include, for example: higher alcohols (e.g., propanol); poly-alcohols (e.g., ethylene glycol; 1,3 propanediol; 1,2,3 propanetriol [glycerol]). The composition of these other primary components (balance primarily water) can vary from about 2-70%, preferably from about 4-50%, and most preferably from about 25-40%, by weight.

The syngas stream 420 preferably is obtained from the zoned partial oxidation (via partial oxidation, or gasification reactions) of biomass in the unit 300. The inputs to unit 300 may include one stream 310, and additionally may include one co-feed stream, or two co-feed streams 340, 350, in which the co-feed 340 is hydrogen-rich or carbon-rich, and the co-feed 350, is an oxidant relative to the conditions of the zoned partial oxidation operation. The co-feed stream 340 may include one or more of coal, petroleum coke, waste (low grade) coal or coke, petroleum, natural gas, co-feeds (with biomass) of additional biomass sources, additional components (e.g., stalks) from same biomass source, etc. The co-feed stream 350 may include one or more of steam, oxygen, and/or air. The composition and specifications of the syngas stream 420 preferably includes CO+$H_2$, combined totaling about 50-100% of this stream 420, preferably from about 80-100%, and most preferably from about 90-100%. The syngas stream 420 also may contain: (a) $CH_4$ in an amount not more than 15% of this stream 420, preferably ≦5%, and most preferably ≦2%; (b) $CO_2$ in an amount not more than 30% of this stream 420, preferably <10%, and most preferably <5%. The $H_2$/CO syngas molar ratio for stream 420 preferably is within the range of from about 1.0-3.0, more preferably from about 1.5-2.5, and most preferably from about 1.8-2.2.

Particularly preferred and exemplary embodiments now will be described with reference to the following non-limiting example.

EXAMPLE

Higher alcohol fuel is produced in two cuts: a butanol cut, specifically isobutanol (also 2-methyl 1-propanol; i-$C_4H_9OH$; here "i-BuOH"), and a cut comprising a mixture of branched pentanols and hexanols, specifically 2-methyl 1-butanol (referred to here as: i-$C_5H_{11}OH$) and 2,2-dimethyl 1-butanol (referred to here as: i-$C_6H_{13}OH$), respectively. This is accomplished from two process intermediates: a corn grain fermentation-derived aqueous ethanol stream, and syngas derived from non-fermentable cellulose with co-feeds of natural gas and steam.

Aqueous ethanol is generated from corn-based carbohydrate fermentation. The fermentation is carried out at atmospheric pressure and 30-32 C, in batch mode for 45-50 hours, following treatment by standard commercial saccharification enzymes. The initial fermentation intermediate is a broth of 12.5 wt. % ethanol (solids-free basis), and is transferred to the fermentation process "beer well" for staging prior to separations. A combined solids settling and single-stage distillation operation is carried out in the "beer column", which provides the function here of primary separations.

The primary separations operation is carried out under vacuum, at 70 C. The yields from this single-stage operation include:
- 41,573 kg/hr aqueous ethanol solution
- 41.0 wt. % ethanol—17,045 kg/hr—equivalent of 50 MM gpy neat ethanol production balance water—24,528 kg/hr
- 94,790 kg/hr bottoms (untreated) water—solids-free basis
- 12,000 kg/hr distiller's grains solids—ultimately deployable dried ("DDGS") as a high-protein, animal feed by-product Synthesis gas is generated by a two-zone, zoned partial oxidation operation—in this instance, tandem fluidized bed gasifiers. The first gasifier is the pyrolysis zone, operated at 900 C and 30 atm pressure. Bulk solids (10-50 mm chips) of non-fermentable cellulosic biomass, available from the same corn feedstock resource, but recovered separately from the grain, are fed via an auger and pressurized lock-hopper injection system. This cellulose is fed to the first zone at 16,080 kg/hr, assuming a combined conversion and utilization factor of 95%.

This biomass feedstock takes many chemical structural forms, but in the aggregate, all of these average an elemental ratio makeup of 1:2:1 C:H:O. They can be accurately represented (for purposes of mass balances and thermodynamics) as simple sugar or starch components with formulas in this ratio.

The second zone of the zoned partial oxidation, also a fluidized bed zone, completes the pyrolysis and also the partial oxidation of the biomass to syngas. It is operated at 1,050 C and 30 atm pressure. Here additional co-feed is added; in the present case, additional hydrogen is needed and is provided via natural gas at 8,162 kg/hr ($CH_4$ equivalent) and 9165 kg/hr process steam (20 atm, superheated to 250 C). This steam provides the needed oxidant for the excess carbon, and the combination of steam and natural gas provides additional syngas with an equivalent $H_2$/CO ratio of 3:0.

Overall, the combined syngas output of the zoned partial oxidation operation is 32,604 kg/hr total syngas, which comprises 28,502 kg/hr CO and 4,102 kg/hr $H_2$. This represents a molar ratio of $H_2$/CO of 2.0, and a molar ratio of "syngas equivalents" (CO+2$H_2$) to ethanol feed of 2.75. Both these factors are desired in this case for the intended product slate of higher alcohols, and are maintained in operation via feedback control. The liquid product composition is measured on-line, and is maintained in desired composition (in this case, the relative amounts of isobutanol, and combined $C_5$-$C_6$ branched products) via on-line adjustments of feed/co-feed amounts and ratios in the zoned partial oxidation operation.

Thus the reactants are fed to the reactive separation operation in the relative mole ratio: 1 EtOH/2.75 CO/5.5 $H_2$. This enables a steady-state average conversion of the ethanol that is equally split (on the basis of the ethanol) between isobutanol product on one hand, and a mixture of i-$C_5H_{11}OH$ and i-$C_6H_{13}OH$ on the other—as desired for the purpose of the fuel products generated for this example case. (Other splits could be achieved through adjustments of the feeds and co-feeds.)

On these bases, the combined feed to the reactive separation unit is approximately as follows:
- 17,046 kg/hr EtOH with 24,529 kg/hr water—at 70 C and 1 atm, pumpable to the pressure of the lower section (see below) of the reactive separations operation (here, 80 atm);
- 28,502 kg/hr CO and 4,102 kg/hr $H_2$, hot-filtered and compressed to 400 C and 80 atm.

The reactive separation operation is carried out using the following mode and conditions:
Pressurized lowest stages; isenthalpic pressure letdown (flash) to upper, vapor-only stages
Number of high-pressure (lowest) stages: 2
Water-rich draw from stage 1
Temperature and pressure in lowest stages: 280 C; 80 atm
Number of upper stages: 8
Temperature and pressure in upper stages: 340 C; 20 atm
Vapor side product draws: i-$C_4H_9OH$; i-$C_5H_{11}OH$ and i-$C_6H_{13}OH$ (combined)

The reactive separations unit is operated under position-dependent conditions, consistent with the operating concept embodied in the mode described above. The lower section is maintained at saturated or sub-saturated conditions with respect to aqueous vapor pressure, and is thus a multi-phase slurry: aqueous reactants, products, and solid catalyst. Here, these bottom 2 stages (i.e., lower section) are maintained at 280 C and 80 atm.

An intermediate, water-rich phase is removed from the bottom section (stage 2), phase-separated, and the water-rich component is partially removed for process recycle (e.g., to fermentation), and partially re-injected to the bottom section (phase 1). An intermediate organic-rich phase is reduced in pressure (flashed) and directed to the remaining stages of the reactive separation.

The remaining stages (upper section) are operated at a lower pressure, and higher temperature—starting at 340 C at its lowest stage, and 20 atm. The catalyst and operating conditions are chosen consistent with known art for the design intent of generating higher, branched mono-alcohols. See, e.g., Herman, R. G., "Advances in Catalytic Synthesis and Utilization of Higher Alcohols", *Catalysis Today*, 55, pp. 233-245 (2000); Olson, E. S., R. K. Sharma and T. R. Aulich, "Higher Alcohols Biorefinery—Improvement of Catalyst for Ethanol Conversion", *Applied Biochemistry and Biotechnology*, 115; 913-932 (2004). The overall reactions in the combination of the reactive separation stages include:

$$2CO + 4H_2 + C_2H_5OH = i\text{-}C_4H_9OH + 2H_2O \quad (1)$$

$$3CO + 6H_2 + C_2H_5OH = i\text{-}C_5H_{11}OH + 3H_2O \quad (2)$$

$$4CO + 8H_2 + C_2H_5OH = i\text{-}C_6H_{13}OH + 4H_2O \quad (3)$$

The product i-BuOH (i-$C_4H_9OH$), synonymous with 2-methyl 1-propanol, is the dominant $C_4$ branched product under these conditions. The higher branched products, i-$C_5H_{11}OH$ and i-$C_6H_{13}OH$, each have several possible and likely present isomers, but these are represented here as 2-methyl 1-butanol, and 2,2 dimethyl 1-butanol, respectively. Each of these species is consistent with the mechanisms and observations found in the cited work, and also affords representative formation thermodynamics (including the reaction heat effects) that are well representative of the full isomer set expected.

Thermodynamically, each of the above reactions is largely favored over the range of temperatures of interest—and also enhanced (shifted, to the right) with higher pressure. Specifically at the conditions cited, the equilibrium constants (Keq) for these overall reactions at 280 C and 340 C are calculated as follows, using the commercially-available package HSC Chemistry® 6.0, and specifically referencing the pure component formation energies and enthalpies as provided by its well-established databases. See Roine, A., *HSC Chemistry®* 6.0, Outokumpu Technology, Pori, Finland; ISBN-13: 978-952-9507-12-2; August 2006.

With these assumptions and the attendant conversion and mass balance calculations, product cut streams of 13,027 kg/hr i-$C_4H_9OH$, and 7,746 kg/hr i-$C_5H_{11}OH$ plus 8,979 kg/hr i-$C_6H_{13}OH$ (combined cut) are achieved, as separate side vapor draws. These product rates are equivalent to 37.6 MM gpy and 47.5 MM gpy, respectively. Additional water removal from these streams will be necessary, and is achievable by means of simple azeotropic distillation, by close analogy to similar systems. See Luyben, W. L., "Control of the Heterogeneous Azeotropic n-Butanol/Water Distillation System," *Energy & Fuels*, 22 (6), 4249-4258, September 2008.

By means of this process, the energy generated by the reactive separation exotherm is enough to fully drive that process, with the complete vaporization of the product streams (at 340 C and 20 atm), along with all the associated water, and also provide some additional excess energy for other intraprocess use. Assuming vapor phase products (both the alcohols, and water) at the system temperature of 340 C, this excess generated (and available) energy is approximately 25,300 Mcal/hr (=100.5 MMBTU/hr=29.5 $MW_{th}$). This can be applied toward the residual azeotropic separations burden, which should be small, and likely even negative in this case (starting with the relatively hot vapor streams). Alternatively, it can be applied to the primary fermentations separation operation (upstream), or other preheating functions—as constrained by the 340 C energy quality.

These two branched alcohol product cuts have particular utility as fuels, intended as gasoline replacements or gasoline additive components.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, this disclosure is intended to be illustrative, but not limiting of the scope of the invention.

| HAS Reaction | Product | Isomer | Keq (280 C.) | Keq (340 C.) | [units] |
|---|---|---|---|---|---|
| (1) | i-$C_4H_9OH$ | 2-Me 1-propanol | $8.35 \times 10^5$ | $1.03 \times 10^3$ | [bar$^{-4}$] |
| (2) | i-$C_5H_{11}OH$ | 2-Me 1-butanol | $8.01 \times 10^7$ | $3.49 \times 10^3$ | [bar$^{-6}$] |
| (3) | i-$C_6H_{13}OH$ | 2,2-di Me 1-butanol | $8.24 \times 10^9$ | $1.07 \times 10^4$ | [bar$^{-8}$] |

As is standard for equilibrium constant calculations and application, this does not take into account transport or kinetic effects, or the influence (via relative kinetics) of competing reactions. For simplicity of illustration, this limited, but representative product slate is assumed.

The combined influence of the equilibrium constant and the pressure effect gives rise to a one-pass (equilibrium) conversion—or limiting one-stage extent of reaction—of at least 0.96 for each of these net reactions and condition sets. The overall yield can be improved to, and even beyond this limit, because of the continuous separation of products, and reflux of reactants—as well as the multistage action with equilibrium approached at each stage. More conservatively here, allowing for losses and/or byproducts, a total conversion of 0.95 is assumed for each of the reactions, relative to the available ethanol, or conversion distribution.

A conversion distribution (on the basis of total ethanol available) of 50% to $C_4$, 50% to $C_5+C_6$ (each, 25%) was assumed based on these competitive thermodynamics and consistent with the available syngas and associated higher alcohol synthesis stoichiometry.

What is claimed is:

1. A method for converting hydrocarbon-containing materials into valuable chemicals, the method comprising:

producing a syngas intermediate comprising hydrogen and CO by zoned partial oxidation and/or gasification of at least a portion of a hydrocarbon-containing material input;

introducing the syngas intermediate into a reactive separation unit;

producing in an alcohol generation unit an alcohol intermediate comprising at least one or more alcohols or aqueous mixtures containing one or more alcohols;

introducing the alcohol intermediate into the reactive separation unit; and chemically reforming the syngas intermediate and the alcohol intermediate in the reactive separation unit to produce at least one product selected from the group consisting of saturated hydrocarbons, higher alcohols, and mixtures thereof.

2. The method of claim 1, wherein the zoned partial oxidation and/or gasification is performed using a molten metal system.

3. The method of claim 1, wherein the zoned partial oxidation and/or gasification is performed using a fluidized bed system.

4. The method of claim 1, wherein the hydrocarbon-containing material input includes a combination of biomass and other hydrocarbon-containing materials.

5. The method of claim 1, wherein the alcohol intermediate is produced by fermentation of biomass.

6. The method of claim 1, further comprising:
introducing at least a portion of bulk solids into the zoned partial oxidation unit, the bulk solids including solid matter greater than 1 mm in size.

7. The method of claim 6, further comprising:
subjecting the hydrocarbon-containing material input to a thermal or pyrolysis pretreatment in a first zone in the zoned partial oxidation unit, the thermal or pyrolysis pretreatment resulting in tars, gases, char, or other solid residuals; and
processing the resultant tars, gases, chars, or other solid residuals in one or more subsequent zones in the zoned partial oxidation unit to produce the syngas.

8. The method of claim 1, further comprising:
gasification processing of supplemental inputs in a zoned partial oxidation unit, the supplemental inputs comprising at least one material selected from the group consisting of: (i) solid byproduct derived from fermentation of biomass after first subjecting an aqueous slurry, fermentation intermediate to coarse solid-liquid separation; (ii) hydrocarbon-containing materials at least partially derived from biomass; (iii) hydrocarbon-containing materials from available waste or other byproduct streams or inventories; (iv) one or more carbon-rich materials; (v) one or more hydrogen-rich materials; and (vi) combinations thereof.

9. The method of claim 8, further comprising:
recombining the syngas intermediate streams generated in the zoned partial oxidation unit so as to achieve a desired $H_2$/CO ratio in the syngas prior to chemically reforming; and
adjusting the rate or composition of the syngas intermediate introduced into the reactive separation unit and adjusting the rate or composition of the supplemental inputs in the zoned partial oxidation unit using feedback control to achieve a final desired product composition.

10. A method for converting hydrocarbon-containing materials into valuable chemicals, the method comprising:
feeding a stream of materials into an alcohol generation unit to produce a first stream of alcohol-containing aqueous intermediate;
subjecting the first stream to primary separations processing in a primary separations unit to remove a mixture of water and solids and to produce a resultant stream of aqueous alcohol;
feeding one or more non-fermentable solid streams into a zoned partial oxidation unit;
introducing a first co-feed stream into the zoned partial oxidation unit, the first co-feed stream comprising a carbon-rich or hydrogen-rich stream;
introducing a second co-feed stream into the zoned partial oxidation unit, the second co-feed stream comprising an oxidant relative to the conditions in the zoned partial oxidation unit;
carrying out one or more processes selected from the group consisting of devolatilization, pyrolysis, and partial oxidation in the zoned partial oxidation unit;
yielding at least one of a hydrogen-rich syngas intermediate output and a CO-rich syngas intermediate output from the zoned partial oxidation unit;
combining or recombining the at least one of hydrogen-rich syngas intermediate output and the CO-rich syngas intermediate output to produce a combined syngas stream;
concurrently introducing the combined syngas stream and the resultant stream of aqueous alcohol into a reactive separation unit, the reactive separation unit subjecting the combined syngas stream and the resultant stream of aqueous alcohol to gas-to-liquid reformation reactions; and
producing a product stream comprising at least one component selected from the group consisting of a higher alcohol liquid, an aliphatic liquid hydrocarbon, and mixtures thereof.

11. The method of claim 10, wherein the first stream of alcohol-containing aqueous intermediate is a bioethanol-water intermediate.

12. The method of claim 10, wherein the removed mixture of water and solids is processed into dried distiller's grains, and the water is recovered, treated and recycled for further fermentation or process uses.

13. The method of claim 10, wherein the gas-to-liquid reformation reaction(s) in the reactive separation unit are accomplished by a process selected from staged reaction and distillation or reactive distillation.

14. The method of claim 10, wherein zoned partial oxidation is carried out using a process selected from fluidized-bed gasification or molten-metal gasification.

15. The method of claim 10, wherein the one or more non-fermentable solids fed into the zoned partial oxidation unit includes additional biomass.

16. The method of claim 15, wherein the additional biomass comprises non-fermentable fractions comprised of one or more components selected from the group consisting of cellulosic material, lignin, byproducts or wastes of pulp or paper processing, and mixtures thereof.

17. The method of claim 10, further comprising:
producing a hydrogen-rich syngas intermediate output and a CO-rich syngas intermediate output from the zoned partial oxidation unit;
recombining the hydrogen-rich syngas intermediate output and the CO-rich syngas intermediate output to produce a combined syngas stream of desired composition prior to introducing the combined syngas stream into the reactive separation unit.

* * * * *

UNITED STATES PATENT AND TRADEMARK OFFICE
CERTIFICATE OF CORRECTION

PATENT NO.       : 7,932,297 B2                                    Page 1 of 1
APPLICATION NO.  : 12/353702
DATED            : April 26, 2011
INVENTOR(S)      : Thomas Paul Griffin It is certified that error appears in the above-identified patent and that said Letters Patent is hereby corrected as shown below:

On the title page:

item (73), Assignee:

delete: "Pennsylvania Sustainable Technologies, LLC Bethlehem, PA"; and
insert: --Logos Technologies, Inc. Arlington, Virginia--.

Signed and Sealed this
Twenty-sixth Day of July, 2011

David J. Kappos
*Director of the United States Patent and Trademark Office*